United States Patent [19]

Dosoretz et al.

[11] Patent Number: 5,604,298
[45] Date of Patent: Feb. 18, 1997

[54] GAS MEASUREMENT SYSTEM

[75] Inventors: Victor J. Dosoretz, Newton Center; Daniel Behr, Needham; Scott Keller, Lincoln, all of Mass.

[73] Assignee: In USA, Inc., Needham, Mass.

[21] Appl. No.: 568,639

[22] Filed: Dec. 7, 1995

[51] Int. Cl.⁶ .............. G06F 15/46; G05D 25/02; G01F 13/00
[52] U.S. Cl. ................ 73/23.2; 73/40.5 R; 73/31.06
[58] Field of Search .................... 73/23.2, 40.5 R, 73/31.06

[56] References Cited

U.S. PATENT DOCUMENTS

| | | | |
|---|---|---|---|
| 2,088,497 | 7/1937 | Tijmstra | 196/13 |
| 2,165,489 | 7/1939 | Kranz | 261/94 |
| 2,759,354 | 8/1956 | Cherry et al. | 73/27 |
| 2,802,109 | 8/1957 | Waters | 250/43.5 |
| 2,899,281 | 8/1959 | Olmer | 23/254 |
| 2,913,386 | 11/1959 | Clark, Jr. | 204/195 |
| 3,153,577 | 10/1964 | McCully et al. | 23/255 |
| 3,193,360 | 7/1965 | Scoggin | 23/283 |
| 3,425,264 | 2/1969 | Frei | 73/40.5 R |
| 3,466,149 | 9/1969 | Blood et al. | 23/283 |
| 3,788,070 | 1/1974 | Camarasa et al. | 60/290 |
| 3,796,657 | 3/1974 | Pretorius et al. | 210/310 |
| 3,812,330 | 5/1974 | Bowman et al. | 235/92 |
| 3,865,967 | 2/1975 | Pritchett | 174/11 R |
| 3,897,153 | 7/1975 | Keenan et al. | 356/51 |
| 3,960,673 | 6/1976 | Morrow et al. | 204/1 |
| 4,065,412 | 12/1977 | Dreyer | 260/8 |
| 4,090,179 | 5/1978 | Hirano | 340/242 |
| 4,118,193 | 10/1978 | Neti et al. | 422/94 |
| 4,167,665 | 9/1979 | Johns et al. | 250/205 |
| 4,203,946 | 5/1980 | Ryerson | 422/98 |
| 4,232,225 | 11/1980 | Randhawa | 250/361 |
| 4,240,799 | 12/1980 | Ryerson | 23/232 |
| 4,314,344 | 2/1982 | Johns et al. | 364/500 |
| 4,343,177 | 8/1982 | Carlon et al. | 73/23 |
| 4,409,183 | 10/1983 | Fischer | 422/68 |
| 4,526,028 | 7/1985 | Hübner | 73/23 |
| 4,687,934 | 8/1987 | Passaro et al. | 250/343 |
| 4,704,256 | 11/1987 | Hood et al. | 422/68 |
| 4,765,280 | 8/1988 | Kobayashi et al. | 122/5.5 |
| 4,849,178 | 7/1989 | Azuma | 422/69 |
| 4,916,079 | 4/1990 | Baillie et al. | 436/174 |
| 4,956,063 | 9/1990 | Hale | 204/153.17 |
| 5,025,653 | 6/1991 | Schuldt | 73/1 G |
| 5,030,334 | 7/1991 | Hale | 204/153.17 |
| 5,060,505 | 10/1991 | Tury et al. | 73/1 G |
| 5,064,506 | 11/1991 | Sparenberg et al. | 203/2 |
| 5,065,613 | 11/1991 | Lehnert et al. | 73/23.2 |
| 5,120,403 | 6/1992 | Smith, Jr. | 203/1 |
| 5,184,017 | 2/1993 | Tury et al. | 250/343 |
| 5,334,536 | 8/1994 | Nonnenmacher | 436/135 |
| 5,365,216 | 11/1994 | Kotwicki et al. | 340/439 |
| 5,382,326 | 1/1995 | Szopinski et al. | 162/238 |
| 5,448,906 | 9/1995 | Cheung | 73/31.06 |

OTHER PUBLICATIONS

Paper entitled: "A Proposed New Analysis For Ozone In Water Using A Field Portable Chemiluminescent Ozone Analyzer", by Sam S. Brody, presented at the First International Symposium on Ozone for Water & Wastewater Treatment, Dec. 2–5, 1973. In USA, Inc. brochure entitled Anseros WP Series Ozone In Water UV or Chemiluminescence Analyzers.

(List continued on next page.)

Primary Examiner—Hezron E. Williams
Assistant Examiner—J. David Wiggins
Attorney, Agent, or Firm—Weingarten, Schurgin, Gagnebin & Hayes LLP

[57] ABSTRACT

A gas measurement system includes a first test unit for measuring the concentration of a selected gas at a first location, a second test unit for measuring the concentration of the selected gas at a second location, and a comparator for comparing the measured concentration of the selected gas from the first location with the measured concentration of the selected gas from the second location. An alarm indication is provided when a difference between the first and second measurements is greater than a user defined value or percentage. In an exemplary embodiment, the gas measurement system is configured to detect an ozone leak.

13 Claims, 1 Drawing Sheet

OTHER PUBLICATIONS

In USA, Inc. brochure entitled "Series IN–2000" Single and Multi–Point Ambient Ozone Analyzer.

In USA, Inc. brochedure entititled "Anseros Ozomat MP" Continous Process UV Ozone Analyzer for Measurement of Ozone in Air at Low & High Concentrations.

In USA, Inc. Afx Ozone Instrumentation brochure entitled "Series W Disolved and Residual Ozone Analyzers".

One page from "Chemical Engineers'Handbook" Fifth Edition, McGraw–Hill Book Company, Packed Columns 18–19.

In USA, Incorporated Operating Manual, Afx Instrumentation entitled: *Model W1 Dissolved Ozone Analyzer*, Version 4.0 Issue 1, May 1995, © 1994, In USA, Inc.

In USA, Incorporated Operating Manual entitled: *Anseros Ozomat WP Installation and Operation Manual*.

GAS MEASUREMENT SYSTEM

FIELD OF THE INVENTION

This invention relates to gas detection and measurement, and more particularly to a method and apparatus for detecting ozone.

BACKGROUND OF THE INVENTION

Spectrochemical analysis includes a number of techniques for determining the presence or concentration of elemental or molecular constituents in a sample through the use of spectrometric measurements. One particular technique, spectrophotometric analysis, is a method of chemical analysis based on the absorption or attenuation of electromagnetic radiation of a specified wavelength or frequency. A spectrophotometer for providing such analysis generally consists of a source of radiation, such as a light bulb; a monochromator containing a prism or grating which disperses the light so that only a limited wavelength, or frequency range is allowed to irradiate the sample; the sample itself; and a detector, such as a photocell, which measures the amount of light transmitted by the sample.

The near ultraviolet spectral region from 200 to 400 nm is commonly used in chemical analysis. Ultraviolet spectrophotometers usually have at least a lamp as a radiation source, a sensor and appropriate optical components. Simple inorganic ions and their complexes as well as organic molecules can be detected and determined in this spectral region.

In most quantitative analytical work, a calibration or standard curve is prepared by measuring the absorption of a known amount of a known absorbing material at the wavelength at which it strongly absorbs. The absorbance of the sample is read directly from the measuring circuit of the spectrophotometer.

Most gasses have at least one well defined peak of absorption at a certain wavelength. For ozone ($O_3$), one peak of absorption is at 253.7 nm, in the ultraviolet range of the spectrum. The concentration of a selected gas in a sample can be obtained by solving an equation, known as the Beer-Lambert equation as follows:

$$I_s = I_r * e^{-\epsilon L C}$$

where:

$I_s$ is the intensity of light from the sample;

$I_r$ is the intensity of light from the reference;

$\epsilon$ is the ozone absorption coefficient constant at the wavelength used;

L is the length of the absorption chamber (path length of the light); and

C is the concentration of gas in weight/volume.

Since L and $\epsilon$ are fixed quantities, gas concentration can be determined by measuring the intensities $I_s$ and $I_r$. The Beer-Lambert equation provides an absolute determination of gas concentration. The relationship requires the measurement of a "reference" light intensity and a "sample" light intensity. In known ozone analyzers, the "sample" and "reference" measurements are typically acquired by alternately detecting the amount of light passing through an absorption chamber, cell, or cuvette containing the gas sample, and the amount of light passing through a sample which does not contain ozone.

Several compounds present in certain industrial applications can absorb light at the same wavelength as ozone. When attempting to measure low levels of ozone, these gasses can cause interference or false ozone readings. In many cases the chemical composition of the interfering gasses is unknown or variable. This presents a severe challenge when attempting to detect ozone leaks from either ozone-producing equipment or tubing that conveys ozone required for process steps or ozone produced by a process.

It is known to house ozone generating equipment within a cabinet capable of containing a gas leak. Ambient air, which may include traces of ozone, can be aspirated through a vent and into the cabinet to cool the ozone generating equipment. The warm air from within the cabinet is continuously exhausted to an ozone destruction or neutralization device, such as a scrubber or catalytic converter. Therefore, should the ozone generating equipment develop an ozone leak, the risk of environmental contamination is reduced. Additionally, the functionality of the device that produces the ozone or the process that requires ozone may be compromised.

To further reduce the risk of ozone escaping from the cabinet and to detect equipment failure, it is desirable to detect an ozone leak as soon as possible. However, known devices that merely detect the presence of ozone or which only perform an absolute concentration measurement are unacceptable because air entering the gas containment cabinet may include ozone in an unknown and possibly a varying amount, as well as other possibly interfering compounds. The amount of ambient ozone is unknown because the distribution of atmospheric ozone is not uniform. It is well known that ozone concentration varies from location to location and changes with the temperature and season. The ambient gas concentration is even affected by the presence of electronic and industrial devices. For example, printers and copiers give off ozone during operation. Accordingly, by comparing an gas concentration value to a static reference value, it is impossible to determine whether the difference between the values is indicative of periodically elevated ambient gas concentrations or to an ozone leak.

SUMMARY OF THE INVENTION

The present invention provides an apparatus and a method for detecting ozone. The invention eliminates the adverse effects of interference from other compounds that render spectrophotometric analysis unreliable and it permits an ozone leak to be detected in an environment that includes an unknown or variable ozone level, or other potentially interfering compounds.

In an exemplary embodiment, a measurement of the concentration of a selected gas, such as ozone, is obtained by sampling air upstream from an ozone generating device and performing a spectrochemical analysis of the sample and comparing it with an ozone free reference gas. Concurrently, a measurement of the concentration of the selected gas is obtained by sampling air flowing downstream from the ozone generating device and performing a spectrochemical analysis of the downstream sample and comparing it with an ozone free reference gas. The upstream and downstream ozone concentrations are constantly or periodically compared. When there is a difference between the first and second concentrations that is greater than a user defined value or percentage, an alarm indication is provided to indicate the presence of an ozone leak.

In another embodiment of the invention, gas from first and second locations flows directly to respective first and second absorption cells. The cells are illuminated, the intensity of light from the samples is registered, and the intensities are compared. A difference between the measured light intensities in the respective absorption cells indicates the presence of a gas leak.

DESCRIPTION OF THE DRAWINGS

Other features and benefits of the invention can be more clearly understood with reference to the specification and the accompanying drawing in which.

DETAILED DESCRIPTION OF THE INVENTION

Figure 1:
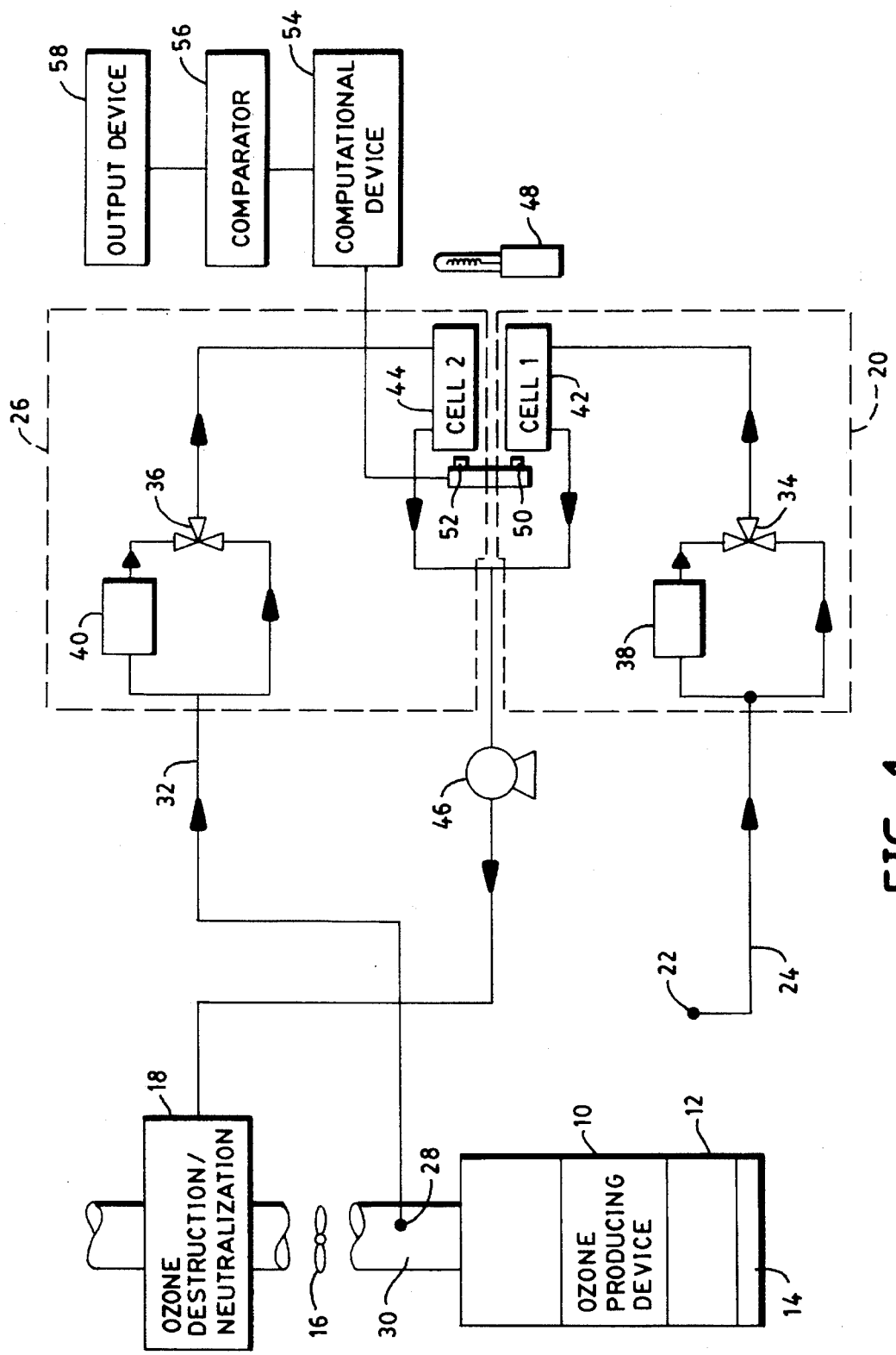
FIG. 1 is a schematic drawing of a gas detection and measurement system in accordance with the invention.

FIG. 1 is a schematic representation of a gas detection and measurement system. Although the system can be configured to detect any substance compatible with gas detection and measurement techniques, the following description relates to an apparatus configured for detecting ozone, and more particularly for detecting ozone leaks.

An ozone producing device 10 is shown positioned within a cabinet 12 that acts as an ozone containment vessel. Exemplary ozone producing devices include ozone generators and pneumatic equipment used in the transmission of ozone gas. The cabinet 12 includes a vent 14 through which ambient air, which may include traces of ozone, or other potentially interfering compounds, can be introduced into the cabinet and pass over, around, or through the ozone producing device 10 to cool it and/or to purge the cabinet 12 of gas. Although ozone produced by the ozone producing device 10 is intended to remain within the device, be neutralized by it, or be conducted in a controlled manner to another location, the possibility exists that ozone may inadvertently escape or leak from the device. Therefore, air from within the cabinet 12 which may further include ozone produced by the ozone producing device 10 is exhausted with the aid of a fan 16 to an ozone destruction or neutralization device 18, such as a scrubber or catalytic converter.

In order to detect ozone leaks, a gas detection and measurement system is provided that includes a first test unit 20 for measuring the concentration of a selected gas at a first location 22. In the exemplary embodiment the selected gas is ozone and the first location is upstream from the ozone producing device 10. For example, the first location 22 can be proximate the vent 14 or a location near the cabinet 12 but exterior thereto in order to be able to sample the ambient air. A first gas conduit 24 is provided for conducting a portion of the upstream gas from the first location to the first test unit.

The gas detection and measurement system further includes a second test unit 26 for measuring the concentration of a selected gas at a second location 28. The selected gas is ozone and the second location 28 is downstream from the ozone producing device 10. For example, the second location 28 can be within an exhaust line or pipe 30 that connects the cabinet 12 to the ozone destruction or neutralization device 18 so that the air exiting the cabinet can be sampled. A second gas conduit 32 is provided for conducting a portion of the downstream gas from the second location 28 within the exhaust pipe 30 to the second test unit 26.

First and second valves 34 and 36 are positionable to cause gas to flow through the respective first and second gas conduits 24 and 32, and thence through respective catalytic converters 38 and 40, before entering respective first and second absorption cells 42 and 44. The catalytic converters 38 and 40 remove ozone from the respective samples so that an ozone free reference gas can be introduced into the respective absorption cells. In an exemplary embodiment, the catalytic converters 38 and 40, as well as the ozone destruction or neutralization device 18, are canisters containing a catalytic material which destroys ozone by converting it into oxygen. An exemplary catalytic material includes $MnO_2$ in pellet form.

The first and second valves 34 and 36 are also positionable to cause the gas flowing through the gas conduits 24 and 32 to bypass the catalytic converters 38 and 40 so that gas samples from the first and second locations 22 and 28 can be provided directly to the respective absorption cells 42 and 44. Thus, the absorption cells 42 and 44 are each alternately fillable with the sample gas and with the ozone free reference gas at a user determined rate.

A pump 46 is provided for drawing gas from the first gas conduit 24 through the first test unit 20 and from the second gas conduit 32 through the second test unit 26. The pump 46 which can be exhausted to the ozone destruction device 18, can be operated to draw gas through the first and second test units, continuously, intermittently, or on demand.

In the illustrated embodiment, the first absorption cell 42 and the second absorption cell 44 are juxtaposed. A single light source 48, such as an ultraviolet lamp, simultaneously illuminates both cells. The intensity of the light passing through each absorption cell 42 and 44 is registered by a first detector 50 associated with the first cell 42 and a second detector 52 associated with the second cell 44. The output of each detector is received by electronics that include a computational device 54 for performing required calculations.

The concentration of ozone at the first and second locations at a given moment is based upon a comparison of the absorption of the reference gas with the sample gas as shown above with respect to the Beer-Lambert equation. A comparator 56 compares the calculated concentration of ozone at the first location with the calculated concentration of ozone at the second location.

The individual test cell measurements, calculations, and comparator output can be presented numerically or graphically on an output device 58 such as a plotter, a printer, or a video display. Other output devices include a signal lamp, an audio producing device, and a mechanical latch. A leak detection signal is provided to one or more output devices when the concentration of the selected gas at the first location differs from the concentration of the selected gas at the second location by either a preset value or by a percentage difference between the concentrations. These parameters can be user selectable.

In another embodiment of the invention, gas from the first and second locations flows directly to the respective first and second absorption cells 42 and 44. The cells are illuminated, the intensity of light from the samples is registered, and the intensities are compared. In this embodiment the test units do not include catalytic converters or another source of a reference gas. Nor is there a process step of comparing the gas from the first and second locations with a reference gas to determine the ozone concentration of the gas at the respective locations. However, as a difference between the measured light intensities in the respective absorption cells can be indicative of different ozone concentrations in each of the cells, such a difference can be indicative of a gas leak.

Although the invention has been shown and described with respect to exemplary embodiments thereof, various other changes, omissions and additions in form and detail thereof may be made therein without departing from the spirit and scope of the invention. For example, although the preceding description has emphasized photochemical gas detection, gas detection and measurement can be provided by other devices. For example, in other embodiments of the invention, the first and second test units 20 and 26 comprise thin or thick film semiconductor devices, or electrochemical sensors instead of absorption cells.

What is claimed is:

1. A gas measurement system comprising:

a first test unit for measuring a concentration of a selected gas $G_s$ in a first mixture of gases from a first location by means of a first detector, said first test unit including
        a first photo absorption cell in fluid communication with said first location,
        a first catalytic converter in fluid communication with said first absorption cell and said first location, and
        a first valve in fluid communication with said first catalytic converter, said first absorption cell and said first location, wherein said first valve is actuatable from a first position to a second position, said first position directing said first mixture of gases through said first catalytic converter and thence to said first absorption cell, and said second position bypassing said first mixture of gases from said first catalytic converter;

a second test unit for measuring a concentration of a selected gas $G_s$ in a second mixture of gases from a second location by means of a second detector, said second test unit including
        a second photo absorption cell in fluid communication with said second location,
        a second catalytic converter in fluid communication with said second absorption cell and said second location, and
        a second valve in fluid communication with said second catalytic converter, said second absorption cell and said second location, wherein said second valve is actuatable from a first position to a second position, said first position directing said selected gas through said second catalytic converter and thence to said second absorption cell, and said second position bypassing said second mixture of gases from said second catalytic converter; and a comparator for receiving outputs from said first and second detectors, and for comparing said concentration of said selected gas $G_s$ from said first location with said concentration of said selected gas $G_s$ from said second location.

2. The system of claim 1, wherein said first test unit includes a first thick film semiconductor sensor in fluid communication with said first location, and said second test unit includes a second thick film semiconductor sensor in fluid communication with said second location.

3. The system of claim 1, wherein said first test unit includes a first thin film semiconductor sensor in fluid communication with said first location, and said second test unit includes a second thin film semiconductor sensor in fluid communication with said second location.

4. The system of claim 1, wherein said first test unit includes a first electrochemical sensor in fluid communication with said first location, and said second test unit includes a second electrochemical sensor in fluid communication with said second location.

5. The system of claim 1, further comprising system electronics including:

a computational device for calculating concentration of said selected gas $G_s$ resident in said first absorption cell and said second absorption cell to determine a concentration of said selected gas $G_s$ at said first location and said second location based upon received outputs from said first and second detectors, and a comparator for comparing said concentration of said selected gas $G_s$ at said first location with said concentration of said selected gas $G_s$ at said second location, wherein said comparator outputs an alarm signal when said concentration of said selected gas $G_s$ at said first location differs from said concentration of said selected gas $G_s$ at said second location.

6. A gas measurement system comprising:

a first test unit for measuring the concentration of a selected gas $G_s$ in a first mixture of gases from a first location by means of a first detector, said first test unit including
        a first photo absorption cell in fluid communication with said first location,
        a first catalytic converter in fluid communication with said first absorption cell and said first location, and
        a first valve in fluid communication with said first catalytic converter, said first absorption cell and said first location, wherein said first valve is actuatable from a first position to a second position, said first position directing said first mixture of gases through said first catalytic converter and thence to said first absorption cell, and said second position bypassing said first mixture of gases from said first catalytic converter;

a second test unit for measuring the concentration of said selected gas $G_s$ in a second mixture of gases from a second location by means of a second detector, said second test unit including
        a second photo absorption cell in fluid communication with said second location,
        a second catalytic converter in fluid communication with said second absorption cell and said second location, and
        a second valve in fluid communication with said second catalytic converter, said second absorption cell and said second location, wherein said second valve is actuatable from a first position to a second position, said first position directing said second mixture of gases through said second catalytic converter and thence to said second absorption cell, and said second position bypassing said second mixture of gases from said second catalytic converter; and system electronics including
        a computational device for calculating concentrations of said selected gas $G_s$ resident in said first absorption cell and said second absorption cell to determine a concentration of said selected gas $G_s$ at said first location and said second location based upon received outputs from said first and second detectors, and
        a comparator for receiving outputs from said first and second detectors, and for comparing said concentration of said selected gas $G_s$ at said first location with said concentration of said selected gas $G_s$ at said second location, wherein said comparator outputs an alarm signal when said concentration of said selected gas $G_s$ at said first location differs from said concentration of said selected gas $G_s$ at said second location.

7. The system of claim 6, further including an output device responsive to said alarm signal.

8. The system of claim 7, wherein said first absorption cell is proximate said second absorption cell, and further comprising a single light source within the optical field of said first absorption cell and said second absorption cell.

9. The system of claim 8, wherein said single light source emits ultraviolet light.

10. The system of claim 9, further comprising a pump for drawing gas from said first location through said first test unit and from said second location through said second test unit.

11. A gas measurement system comprising:
   a cabinet including
      a vent for introducing ambient air into said cabinet,
      an exhaust through which said air within said cabinet is exhausted from said cabinet, and
      an gas producing device for producing a gas $G_s$, said device situated between said vent and said exhaust;
   a first test unit including an absorption spectrophotometer for measuring the concentration of gas $G_s$;
   a first gas conduit for conducting a first mixture of gases from a first location upstream from said gas producing device to said first test unit;
   a second test unit including an absorption spectrophotometer for measuring the concentration of gas $G_s$;
   a second gas conduit for conducting a second mixture of gases from a second location downstream from said gas producing device to said second test unit;
   a comparator for comparing gas $G_s$ concentration at said first location and gas $G_s$ concentration at said second location; and
   a pump for drawing said mixtures of gases from said first gas conduit through said first test unit and from said second gas conduit through said second test unit.

12. The system of claim 11, wherein said comparator outputs an alarm signal when said gas $G_s$ concentration at said first location differs from said gas $G_s$ concentration at said second location.

13. The system of claim 12, further including an output device responsive to said alarm signal.

* * * * *